United States Patent [19]

Habermeier

[11] 4,122,276

[45] Oct. 24, 1978

[54] DICARBOXYLIC ACIDS AND DICARBOXYLIC ACID ESTERS CONTAINING A HETEROCYCLIC RADICAL

[75] Inventor: Jürgen Habermeier, Pfeffingen, Switzerland

[73] Assignee: Ciba-Geigy Corporation, Ardsley, N.Y.

[21] Appl. No.: 794,693

[22] Filed: May 6, 1977

[30] Foreign Application Priority Data

May 12, 1976 [CH] Switzerland ............................ 5933/76

[51] Int. Cl.² ................................................ C07D 233/64
[52] U.S. Cl. ........................................................ 548/310
[58] Field of Search ........................................... 548/310

[56] References Cited

U.S. PATENT DOCUMENTS

| | | | |
|---|---|---|---|
| 3,684,774 | 8/1972 | Merten et al. | 548/310 |
| 3,809,696 | 5/1974 | Porret et al. | 548/310 X |
| 3,946,033 | 3/1976 | Iwata et al. | 548/310 |

OTHER PUBLICATIONS

Sato, Chemical Abstracts, vol. 59 (1963), 3907e.
Derwent Abstract 47300x/25 of Dutch Patent 75/13,582.

*Primary Examiner*—Richard L. Raymond
*Attorney, Agent, or Firm*—Luther A. R. Hall

[57] ABSTRACT

Dicarboxylic acids and dicarboxylic acid esters of the formula

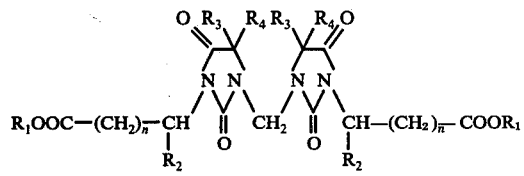

wherein both $R_1$ each denote hydrogen, alkyl with 1 to 4 C atoms or phenyl, both $R_2$ each denote hydrogen or alkyl with 1 to 10 C atoms and, if the two $R_2$ each denote hydrogen, the two $n$ represent numbers from 2 to 12 and, if the two $R_2$ each denote an alkyl group with 1 to 10 C atoms, the two $n$ represent numbers from 1 to 12, $R_3$ denotes hydrogen, methyl or ethyl and $R_4$ denotes methyl, ethyl, propyl or isopropyl, are prepared by reacting 1 mol of a 1,1'-methylene-bis-hydantoin of the formula

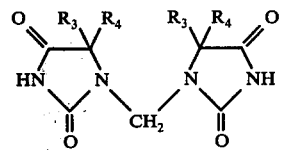

or its disodium or dipotassium salt with 2 mols of a compound of the formula

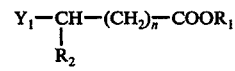

wherein $Y_1$ denotes a chlorine or bromine atom. The dicarboxylic acid compounds are characterized by a high stability to heat and therefore very suitable for the manufacture of polycondensates by the melt condensation process.

13 Claims, No Drawings

DICARBOXYLIC ACIDS AND DICARBOXYLIC ACID ESTERS CONTAINING A HETEROCYCLIC RADICAL

The present invention relates to new aliphatic dicarboxylic acids and dicarboxylic acid esters which contain a 1,1'-methylene-bis-hydantoin radical and to processes for their manufacture.

Dicarboxylic acids which contain a N,N-heterocyclic radical in the molecule are already known. Thus, the manufacture of dicarboxylic acids containing hydantoin and alkylene-bis-hydantoins by the cyanoethylation of hydantoin and alkylene-bis-hydantoins and subsequent hydrolysis of the resulting cyanoethyl compounds to give the dicarboxylic acids is described in "Chemical Abstracts," Volume 59, page 3907(e). These dicarboxylic acids are, however, subject to the disadvantage that they do not have a high stability to heat and, on further processing under warm conditions, for example during the manufacture of polyesters by the melt condensation process, readily redissociate into the hydantoin and acrylic compounds (retro-Michael reaction).

Furthermore, the manufacture of oligohydantoins and polyhydantoins which contain carboxylic acid groups by the reaction of polyglycine esters with isocyanates containing carboxylic acid groups is described in DT-OS No. 1,906,492 and DT-OS No. 2,358,437. These manufacturing processes are, on the one hand, subject to the disadvantage that the necessary starting materials for these processes are obtained only by means of expensive syntheses and that the reaction of the polyglycine esters with the isocyanates, which proceeds with cyclisation, requires relatively high temperatures and, moreover, the desired substances have to be separated off, from the reaction mixture, from products in which cyclisation is not quantitative. On the other hand, because of the lack of a corresponding polyglycine ester, it is not possible to manufacture 1,1'-methylene-bis-hydantoins containing carboxylic acid groups by the processes described in the two DT-OS.

It has now been found that new compounds which contain carboxylic acid groups and which are distinguished by high stability to heat and are thus particularly suitable for the manufacture of polycondensation products by the melt condensation process are obtained in an economically more simple manner by reacting 1,1'-methylene-bis-hydantoins with longer-chain aliphatic halogenocarboxylic acids or halogenocarboxylic acid esters.

The present invention thus relates to new dicarboxylic acids and dicarboxylic acid esters of the formula I

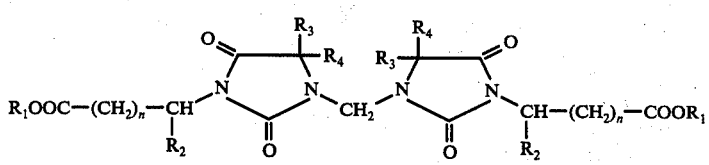

(I)

in which the two $R_1$ s independently of one another each denote a hydrogen atom, an alkyl group with 1 to 4 C atoms or a phenyl group, the two $R_2$ s each denote a hydrogen atom or an alkyl group with 1 to 10 C atoms and, if the two $R_2$ s each denote a hydrogen atom, and two $n$ s represent identical or different numbers from 2 to 12 and, if the two $R_2$ s each denote an alkyl group with 1 to 10 C atoms, the two $n$ s represent identical or different numbers from 1 to 12, $R_3$ represents a hydrogen atom or the methyl or ethyl group and $R_4$ represents the methyl, ethyl, propyl or isopropyl group.

Preferably, in formula I, the two $R_1$ s independently of one another each denote a hydrogen atom, an alkyl group with 1 to 4 C atoms or a phenyl group, the two $R_2$ s independently of one another each denote a hydrogen atom or an alkyl group with 1 to 10 C atoms, $R_3$ represents a hydrogen atom or the methyl or ethyl group and $R_4$ represents the methyl, ethyl, propyl or isopropyl group and the two n s represent identical or different numbers from 2 to 12.

In particular, in formula I, $R_1$ denotes an alkyl group with 1 to 4 C atoms or a phenyl group, $R_2$ denotes a hydrogen atom and n denotes a number from 2 to 4.

These dicarboxylic acid diesters of the formula I in which $R_1$ denotes the methyl, ethyl or phenyl group, $R_2$ denotes a hydrogen atom, $R_3$ denotes the methyl group, $R_4$ denotes the methyl or ethyl group and $n$ denotes from 2 to 4 are of particular interest.

The new dicarboxylic acids and dicarboxylic acid esters of the formula I can be manufactured by reacting 1 mol of a 1,1'-methylene-bis-hydantoin of the formula II

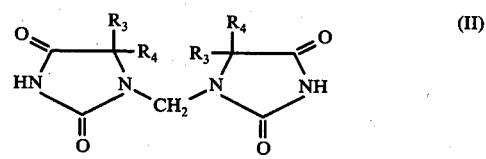

(II)

or the disodium or dipotassium salts thereof, in which $R_3$ and $R_4$ have the same meaning as in formula I, with 2 mols of a compound of the formula III

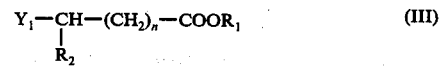

(III)

or mixtures of compounds of the formula III, in which $R_1$, $R_2$ and $n$ have the same meaning as in formula I and $Y_1$ represents a chlorine or bromine atom, with the elimination of 2 mols of hydrogen chloride or hydrogen bromide or of sodium chloride or sodium bromide or of potassium chloride or potassium bromide, to give compounds of the formula I.

Amongst the 1,1'-methylene-bis-hydantoins, those of the formula II in which $R_3$ represents the methyl group and $R_4$ represents the methyl or ethyl group are preferably used.

The ω-chloro- or ω-bromo-carboxylic acid alkyl esters, especially the ω-chlorocarboxylic acid alkyl esters, are preferably used as the compound of the formula III, that is to say the compounds used are compounds of the formula III in which $R_1$ denotes an alkyl group with 1 to 4 C atoms or a phenyl group, especially the methyl, ethyl or phenyl group, $R_2$ denotes a hydrogen atom, $n$ denotes a number from 2 to 4 and $Y_1$ denotes a chlorine or bromine atom, especially a chlorine atom.

In a preferred embodiment, the methyl or ethyl ester of γ-chlorobutyric acid or δ-chlorovaleric acid is used as the compound of the formula III.

As a rule, the conversion reaction is carried out in an organic solvent and the halogen-containing compounds of the formula III are preferably employed in a slight molar excess.

Solvents which can be used are, for example: dimethylformamide, dimethylacetamide, dimethylsulphoxide, N-methylpyrrolidone, tetramethylurea, benzene, toluene, xylene, chloroform and mixtures of such solvents.

It is also possible to carry out the conversion reaction without a solvent, that is to say in the melt. The reaction which proceeds with the elimination of hydrogen halide is appropriately carried out in the presence of an acid acceptor, which is added to the solvent in amounts which at least correspond to the equivalent amount, relative to the calculated amount of hydrogen halide liberated. Acid acceptors suitable for this purpose are, in particular, potassium carbonate, sodium carbonate and calcium carbonate, sodium bicarbonate and also sterically hindered amines, such as N-methylaniline, dimethylaniline and diazabicyclooctane, or also pyridine, tetramethylammonium hydroxide, alkali metal halides and alkaline earth metal halides. The conversion reactions are carried out in the temperature range of 20° to 200° C. and preferably of 50° to 150° C., the reaction temperatures to be chosen depending on the nature of the starting materials, on the composition of the solvent mixture and on the nature of the acid acceptors. In the case of the preferred embodiment, the conversion reaction is carried out at temperatures rising from 60° to 130° C. or at constant temperatures between 75° C. and 130° C.

In a preferred embodiment of the process, the starting materials are employed in the theoretical molar ratio of 1:2, a mixture of dimethylformamide and benzene in a mixing ratio of 1:2 is used as the solvent and sodium carbonate or potassium carbonate is used as the acid acceptor. The water formed during the neutralisation reaction is continuously removed from the batch, by means of the azeotrope with benzene or toluene, and separated off.

In order to isolate the reaction product, the reaction solution is filtered hot in order to remove the potassium halide formed when, for example, potassium carbonate is used as the acid acceptor and the desired product is obtained by allowing it to crystallise out from the reaction solution or by pouring the solution into water and precipitating the product or by concentrating the reaction solution to dryness and recrystallising the crude product from an organic solvent. Various organic solvents, such as, for example, methanol, acetone, ethanol or tetrahydrofurane, are suitable for this purpose.

When the 1,1'-methylene-bis-hydantoins of the formula II are used in the form of their disodium salts or dipotassium salts, these are first rendered anhydrous by vigorous drying and then appropriately suspended in a polar, aprotic solvent, 2 to 2.2 mols of a compound of the formula III being employed per 1 mol of disodium salt or dipotassium salt. The reaction can take place at temperatures between 20° and 180° C. Preferably, the conversion reaction is carried out in the temperature range of 60° to 130° C. The reaction solution is then worked up in the same way as described above.

The 1,1'-methylene-bis-hydantoins of the formula II are known from the literature (see, for example, U.S. Pat. Nos. 2,417,999, 2,418,000 and 3,296,208).

The halogenocarboxylic acids and halogenocarboxylic acid alkyl esters of the formula III are also known from the literature. ω-Halogenocarboxylic acids and their alkyl esters, of the formula III, in which $R_2$ represents a hydrogen atom, are advantageously manufactured by the process described in "Houben-Weyl", Methoden der oganischen Chemie (Methods of Organic Chemistry), Volume 5/3, page 828 (1962) by splitting suitable lactones using, for example, hydrogen chloride and optionally at the same time esterifying the resulting ω-chlorocarboxylic acid with the corresponding alcohol.

Halogenocarboxylic acids and their alkyl esters, of the formula III, in which $R_2$ represents an alkyl group or, optionally, a hydrogen atom can be manufactured by an addition reaction of HBr or HCl with mono-unsaturated aliphatic monocarboxylic acids and optional subsequent esterification of the reaction product, the corresponding halogenocarboxylic acids or mixtures of isomeric halogenocarboxylic acids being formed depending on the position of the double bond in the unsaturated monocarboxylic acid and on the addition mechanism which takes place (Markownikoff's rule). Thus, for example, the addition reaction of HBr with oleic acid or elaidic acid gives a mixture of isomers consisting of 8-bromo- and 9-bromo-stearic acid. In the same way, an addition reaction of HBr with erucic acid or brassidic acid gives a mixture of isomers consisting of 12-bromo- and 13-bromo-behenic acid.

The dicarboxylic acid derivatives according to the invention are colourless viscous liquids or crystalline substances which melt between 35° and 250° C. and are readily soluble in organic solvents but are insoluble or only very slightly soluble in water.

The new dicarboxylic acid derivatives are valuable monomers which are suitable for the manufacture of thermostable plastics. Thus, for example, the dicarboxylic acids and dicarboxylic acid dialkyl esters can be converted, by means of diols, into polyesters which have very valuable mechanical properties. The diglycidyl esters obtained from the dicarboxylic acids by glycidylation with an epihalogenohydrin can also be cured to give epoxide resins which have valuable mechanical properties. The dicarboxylic acids according to the invention are also suitable for modifying curable mixtures consisting of epoxide resins and carboxylic acid anhydrides.

EXAMPLE 1:
1,1'-Methylene-bis-[3-(3'-methoxycarbonyl-n-propyl)-5,5-dimethylhydantoin]

A mixture of 93.7 g (0.35 mol) of 1,1'-methylene-bis-(5,5-dimethylhydantoin), 100.5 g (0.735 mol) of methyl γ-chlorobutyrate, 53.2 g (0.385 mol) of potassium carbonate, 600 ml of N,N-dimethylformamide and 400 ml of benzene is warmed to 101° C. in the course of 30 minutes, whilst stirring, in a glass stirred apparatus which is provided with a thermometer and a water separator with a reflux condenser. The water/benzene azeotrope starts to distil. In the course of 7 hours 8.0 ml of water separate off. The mixture is cooled to 75° C. and the potassium chloride which has formed is filtered off. The filtrate is then evaporated to dryness at 80° C. in vacuo; the residue is then dried to constant weight at 90° C. under 0.5 mm Hg. The crude product is obtained in 100% yield in the form of a virtually colourless viscous liquid which crystallises through completely on standing.

For purification, the product is recrystallised from 150 ml of methanol and after working up and drying 133.2 g (81.3% of theory) of colourless, shiny crystals which melt at 85.2° C. to 85.8° C. are obtained. A further 9.1 g of the product with a melting point of 84°–85.2° C. can be obtained from the mother liquor. The total yield of pure product is thus 86.8% of theory.

Both elementary analysis and the H-NMR spectrum are in accord with the composition $C_{21}H_{32}N_4O_8$ and with the following structure:

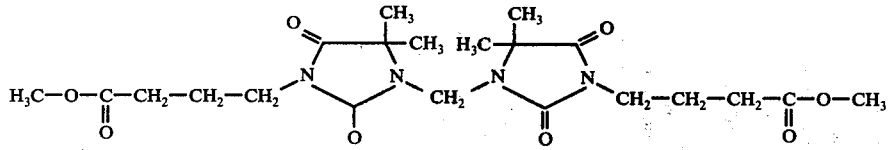

Comparison example 1,1'-Methylene-bis-[3-(3'-methoxycarbonyl-n-propyl)-5,5-dimethylhydantoin] according to Example 1 and the diethyl ester of 1,1'-methylene-bis-[3-(2'-carboxyethyl)-5,5-dimethylhydantoin] according to "Chemical Abstracts", Volume 59, page 3907(e), which is used for comparison, are subjected to heating at 200° C. for several hours; the two compounds have the same molecular weights. The results obtained are compared in the table which follows.

Table

| Compound | according to "Chemical Abstracts" Volume 59, page 3907(e) | according to Example 1 |
|---|---|---|
| Structural formula | $H_5C_2O-CO-CH_2-CH_2-N$ [hydantoin-CH$_2$-hydantoin] $N-CH_2-CH_2-C-OC_2H_5$ | $H_3C-O-CO-CH_2-CH_2-N$ [hydantoin-CH$_2$-hydantoin] $N-CH_2-CH_2-C-O-CH_3$ |
| Empirical formula | $C_{21}H_{32}N_4O_8$ | $C_{21}H_{32}N_4O_8$ |
| Molecular weight | 468.51 | 468.51 |
| Loss in weight at 200° C | | |
| after 30 minutes | 2.24% by weight | 0.39% by weight |
| after 4 hours | 3.56% by weight | 0.41% by weight |
| after 14 hours | 20.28% by weight | 1.10% by weight |
| Indication for retro-Michael reaction: | $N_3$—H signals in the residue detectable by the H—NMR spectrum | no N—H signals in the residue detectable by the H—NMR spectrum |

It can be seen from the table that the compound according to the invention is not only less volatile but does not undergo chemical decomposition on exposure to heat for several hours at 200° C. On the other hand, on identical exposure to heat, the sample taken for comparison has, according to H-NMR spectral analysis, been substantially decomposed by the elimination of

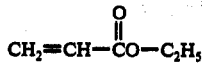

(retro-Michael reaction) and thus, because of the lack of adequate stability to heat, is unsuitable for the manufacture of polycondensation products by the melt process.

of methyl γ-chlorobutyrate and 15.2 g of potassium carbonate powder in 100 ml of benzene and 150 ml of N,N-dimethylformamide are reacted for 4½ hours at 97°–98° C. The reaction solution is worked up as described in Example 1 and 48.6 g (98% of theory) of a glass-clear, virtually colourless, highly viscous product are obtained.

Elementary analysis for $C_{23}H_{36}N_4O_8$:

| found: | calculated: |
|---|---|
| 55.60% C | 55.63% C |
| 7.50% H | 7.31% H |
| 11.20% N | 11.25% N |

The product has the following structural formula:

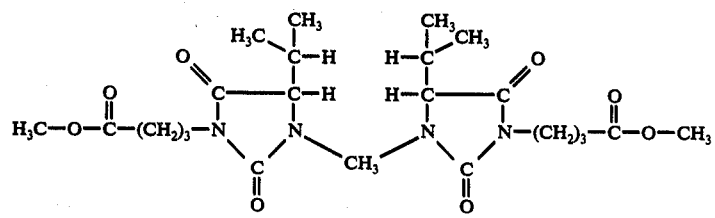

EXAMPLE 2:
1,1'-Methylene-bis-[3-(3'-phenoxycarbonyl-n-propyl)-5,5-dimethylhydantoin]

The following reaction mixture is treated, in accordance with Example 1, for 6 hours at 99°–101° C. with circulatory distillation: 33.53 g (0.125 mol) of 1,1'-methylene-bis-(5,5-dimethylhydantoin), 52.15 g (0.2626 mol) of phenyl γ-chlorobutyrate, 19.0 g (0.1375 mol) of dry potassium carbonate powder, 200 ml of N,N-dimethylformamide and 150 ml of benzene.

After the reaction and working up analogously to Example 1, 69.9 g (94.4% of theory) of a clear, highly viscous liquid are obtained and elementary analysis of this for $C_{31}H_{36}N_4O_8$ gives the following values:

| found: | calculated: |
|---|---|
| 62.80% C | 62.83% C |
| 6.11% H | 6.12% H |
| 9.40% N | 9.45% N |

The 60 Mc H-NMR spectrum is also in agreement with the structure given below:

EXAMPLE 4:
1,1'-Methylene-bis-[3-(3'-ethoxycarbonyl-n-propyl)-5,5-dimethylhydantoin]

In accordance with Example 1, 93.7 g (0.35 mol) of 1,1'-methylene-bis-(5,5-dimethylhydantoin), 110.8 g (0.735 mol) of ethyl γ-chlorobutyrate and 53.2 g (0.385 mol) of potassium carbonate in 550 ml of N,N-dimethylformamide and 400 ml of benzene are reacted for 6½ hours. The working up and isolation of the diester are carried out as described in Example 1. 173.6 g of a colourless, viscous liquid are obtained in 100% yield and this crystallises completely after a short time.

For purification, the crude crystalline product can be recrystallised from 250 ml of methanol. The pure product (113 g) is obtained in 65% yield (without working up of the mother liquor). The colourless crystalline product melts at 66°–68° C.

Elementary analysis for $C_{23}H_{36}N_4O_8$ gives:

| found: | calculated: |
|---|---|
| 55.54% C | 55.63% C |
| 7.23% H | 7.30% H |
| 11.30% N | 11.28% N |

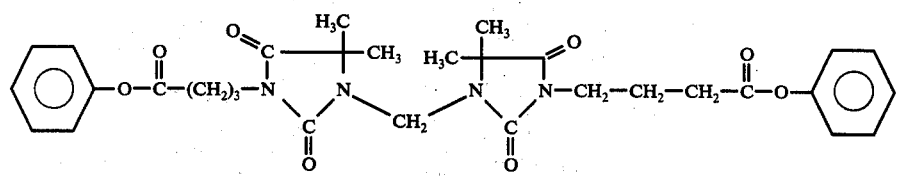

EXAMPLE 3:
1,1'-Methylene-bis-[3-(3'-methoxycarbonyl-n-propyl)-5-isopropylhydantoin]

Analogously to Example 1, 29.6 g (0.1 mol) of 1,1'-methylene-bis-(5-isopropylhydantoin), 28.7 g (0.21 mol)

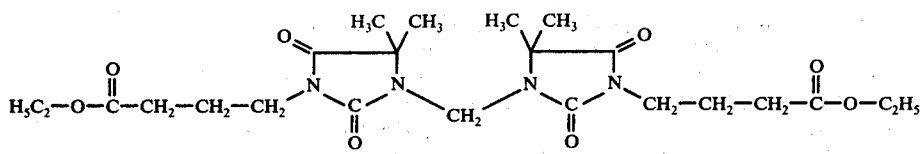

EXAMPLE 5:
1,1'-Methylene-bis-[3-(4'-methoxycarbonyl-n-butyl)-5,5-dimethylhydantoin]

A mixture of 107.2 g (0.4 mol) of 1,1'-methylene-bis-(5,5-dimethylhydantoin), 126.5 g (0.84 mol) of methyl δ-chlorovalerate and 60.8 g (0.44 mol) of potassium carbonate in 600 ml of N,N-dimethylformamide and 400 ml of benzene is reacted according to Example 1. After a reaction time of 5 hours at 98°–101° C., the reaction mixture is worked up in accordance with Example 1. This gives 183.2 g (92.2% of theory) of a colourless to slightly yellowish viscous product, the 60 Mc H-NMR spectrum of which confirms the structure given below. In order to obtain a very pure product, the crude product can be distilled through a thin-film evaporator: boiling point$_{0.1}$ = 290° C.

Elementary analysis of this product for $C_{23}H_{36}N_4O_8$ gives

| found: | calculated: |
|---|---|
| 55.51% C | 55.63% C |
| 7.32% H | 7.31% H |
| 11.32% N | 11.28% N |

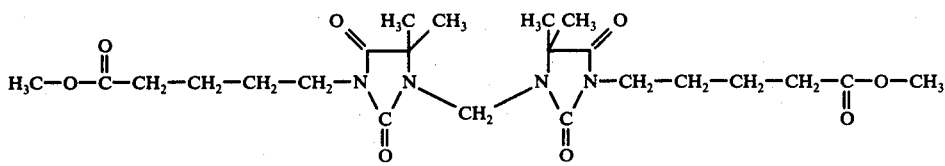

EXAMPLE 6:
1,1'-Methylene-bis-[3-(10'-methoxycarbonyl-n-decyl)-5,5-dimethylhydantoin]

A mixture of 26.8 g (0.1 mol) of 1,1'-methylene-bis-(5,5-dimethylhydantoin), 58.6 g (0.21 mol) of methyl ω-bromoundecanecarboxylate, 15.2 g (0.11 mol) of potassium carbonate and 170 ml of N,N-dimethylformamide and 120 ml of benzene is stirred for 6 hours at 102°–105° C. and at the same time is subjected to circulatory distillation. 2.6 ml of water separate off. The reaction mixture is filtered whilst still hot and the filtrate is concentrated. In order to separate off salt residues and the like, the product is stirred in 100 ml of ether, the mixture is filtered and the filtrate is concentrated. This gives 66.3 g (99.7% of theory) of a pale yellow, highly viscous substance which according to elementary analysis is the desired product.

Microanalysis for $C_{35}H_{60}N_4O_8$

| found: | calculated: |
|---|---|
| 63.20% C | 63.23% C |
| 9.04% H | 9.10% H |
| 8.24% N | 8.43% N |

The H-NMR spectrum is in agreement with the structure given below.

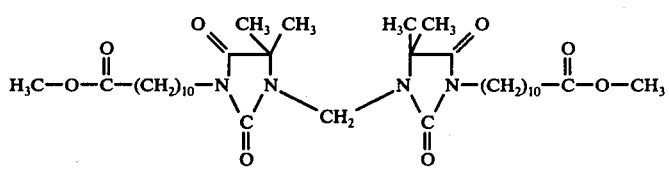

The viscous product gradually crystallises completely on standing. A very pure product can be obtained by recrystallising this substance from hexane; it then melts at 48°–49.5° C.

EXAMPLE 7:
1,1'-Methylene-bis-[3-(5'-methoxycarbonyl-n-pentyl)-5,5-dimethylhydantoin]

A mixture of 26.8 g (0.1 mol) of 1,1'-methylene-bis-(5,5-dimethylhydantoin), 44.0 g (0.21 mol) of methyl 6-bromohexanoate and 15.2 g of dried, powdered potassium carbonate is suspended in a solvent mixture consisting of 150 ml of dimethylformamide and 100 ml of benzene and the suspension is stirred at room temperature. The reaction mixture is warmed to the reaction temperature of 99°–102° C. whilst stirring vigorously and the water formed during the reaction is removed in the course of 12 hours by azeotropic circulatory distillation.

The reaction mixture is filtered whilst still warm and the filtrate is concentrated to dryness. The residue is dissolved in 100 ml of ether and 10 ml of methanol, the solution is filtered and the filtrate is again concentrated to dryness. This gives 50.8 g (96.7% of theory) of the desired crude product in the form of a pale yellow, clear resin.

For purification, the product can be dissolved in ether (petroleum ether, 3:1). After filtering the solution and concentrating the filtrate to dryness under a high vacuum, a purified product which has the following microanalytical data (for $C_{25}H_{40}N_4O_8$), is obtained.

| found: | calculated: |
|---|---|
| 10.80% N | 10.68% N |
| 7.80% H | 7.68% H |

| found: | calculated: |
|---|---|
| 8.36% H | 8.33% H |
| 9.97% N | 9.65% N |

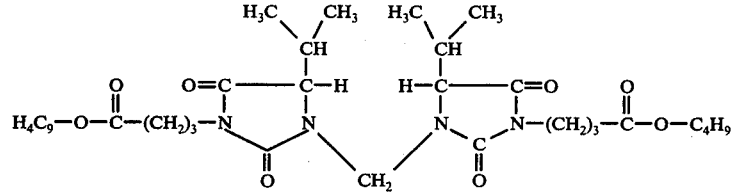

The H-NMR spectrum is also in agreement with the structure given below:

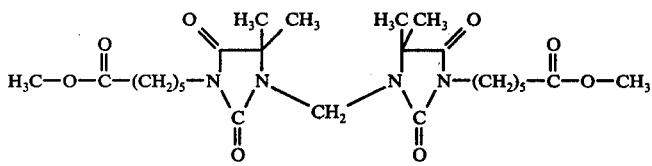

EXAMPLE 8:
1,1'-Methylene-bis-[3-(3'-butoxycarbonyl-n-propyl)-5-isopropylhydantoin]

29.6 g (0.1 mol) of 1,1'-methylene-bis-(5-isopropylhydantoin) are subjected to a condensation reaction with 35.8 g (0.21 mol) of butyl 4-chlorobutyrate with the aid of 15.2 g (0.11 mol) of dry potassium carbonate powder as the acid acceptor. A mixture consisting of 150 ml of dimethylformamide and 150 ml of benzene is therefore used as the solvent. The reaction is carried out at 98°–100° C. with vigorous stirring and continuous removal from the system of the water formed during the reaction. The reaction has ended after 6 hours and the reaction mixture is filtered hot. After concentrating the filtrate, 56.4 g (97% of theory) of the desired product are obtained in the form of a clear, yellowish viscous oil.

For purification, the product is dissolved in 150 ml of ether, the impurities, which consist of salt residues and starting material, are filtered off, the filtrate is concentrated to dryness and the residue is treated to constant weight at 110° C./0.2 mm Hg.

This gives 54.5 g (93.8% of theory) of the pure product in the form of a virtually colourless, clear viscous oil.

The H-NMR spectrum is in agreement with the structure given below. Elementary analysis for $C_{29}H_{48}N_4O_8$ gives:

| found: | calculated: |
|---|---|
| 60.16% C | 59.98% C |

EXAMPLE 9:
1,1'-Methylene-bis-[3-(1'-dodecyl-1'-methoxycarbonyl-methyl)-5,5-dimethylhydantoin]

A mixture of 18.77 g (0.07 mol) of 1,1'-methylene-bis-(5,5-dimethylhydantoin), 10.63 g (0.077 mol) of dry potassium carbonate powder and 47.2 g (0.147 mol) of methyl 2-bromotetradecanoate is initially introduced into 100 ml of dimethylformamide and 80 ml of benzene. The mixture is warmed to 103°–106° C., whilst stirring, and the water formed during the reaction is removed from the system. The reaction is ended after 7 hours and the reaction mixture is filtered whilst still hot. The filtrate is concentrated to dryness and this gives the crude product in quantitative yield as a yellowish oil (52.4 g). For purification, the product is mixed with 40 ml of ether, the mixture is filtered, the filtrate is concentrated and the residue is treated to constant weight at 120° C./0.3 mm Hg. This gives 52.2 g (99.6% of theory) of the purified product in the form of a pale yellow oil which crystallises slowly.

In order to obtain a highly pure product, the substance can be recrystallised from 150 ml of methanol.

This gives colourless crystals with a melting point of 36°–38° C.

The H-NMR spectrum is in agreement with the structure given below. Combustion analysis for $C_{41}H_{72}N_4O_8$ gives

| found: | calculated: |
|---|---|
| 65.85% C | 65.74% C |
| 9.71% H | 9.69% H |
| 7.40% N | 7.48% N |

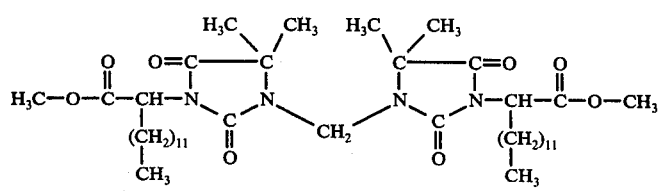

EXAMPLE I: Copolyethylene terephthalate containing 10 mol % of 1,1'-methylene-bis-[3-(3'-methoxycarbonyl-n-propyl)-5,5-dimethylhydantoin]

A mixture of 34.96 g (0.18 mol) of dimethyl terephthalate, 9.37 g (0.02 mol) of 1,1'-methylene-bis-[3-(3'-methoxycarbonyl-n-propyl)-5,5-dimethylhydantoin] and 33.5 g (0.54 mol) of ethylene glycol is trans-esterified at 160° C. to 200° C. in the course of 1.5 hours under the action of a catalyst mixture consisting of 0.03 g of calcium acetate, 0.04 g of zinc acetate and 0.02 g of manganese-II acetate, the methanol formed being removed by distillation. 0.1 g of antimony trioxide is then added and the polycondensation reaction, which now follows, is carried out in the following manner:

2 hours at 200° C.–245° C./normal pressure, $N_2$ atmosphere,
45 minutes at 245° C.–285° C./200 mm Hg–15 mm Hg/$N_2$ and
40 minutes at 285° C.–295° C./15 mm Hg to 0.2 mm Hg/$N_2$.

A colourless to pale yellow partially crystalline product, the relative viscosity of which (measured at 30° C. in a solution consisting of equal parts of phenol and tetrachloroethane) is 1.56 and the Kofler softening point of which is 165° C. is obtained in this way. The copolyester has a glass transition temperature of 60° to 70° C., a crystallite melting point of 224° C. and a decomposition temperature of about 360° C.

EXAMPLE II: Copolyethylene terephthalate containing 30 mol % of 1,1'-methylene-bis-[3-(10'-methoxycarbonyl-n-decyl)-5,5-dimethylhydantoin]

The mixture which follows is trans-esterified for 2 hours at 150°–200° C. under the action of a catalyst mixture consisting of 0.04 g of calcium acetate, 0.05 g of zinc acetate and 0.02 g of manganese-II acetate, methanol being distilled off: 27.19 g (0.14 mol) of dimethyl terephthalate, 39.89 g (0.06 mol) of 1,1'-methylene-bis-[3-(10'-methoxycarbonyl-n-decyl)-5,5-dimethylhydantoin] and 33.50 g (0.54 mol) of ethylene glycol.

0.1 g of antimony trioxide is then added and the polycondensation reaction is started by heating the mixture to 240° C. in the course of 2 hours, ethylene glycol being split off and distilled off. A vacuum is then applied and the temperature is further increased:

45 minutes at 240° → 290° C./200 mm Hg → 15 mm Hg and
30 minutes at 290° C./15 mm Hg → 0.22 mm Hg.

A colourless, transparent, highly viscous copolyester which becomes partially crystalline on stretching is obtained in quantitative yield.

The amorphous product softens at 50° C. and has a relative viscosity, measured at 30° C. in a solution consisting of equal parts of phenol and tetrachloroethane, of 2.03.

Glass transition ranges (DSC 2B): 15°–29° C.
crystallite melting point (DSC 2B): 168°–171° C.
decomposition temperature (DSC 2B): about 350° C.

The product is processed in the customary manner by means of a screw injection moulding machine (Arburg Allrounder 100 M) to standard small bars which have the following properties:

impact bending strength (DIN 53,453): no break
tensile strength (DIN 53,455): 35 kp/cm$^2$
elongation at break (DIN 53,455): 288%

The results show that this copolyester has a very high toughness which, with the incorporation of only 30 mol % of comonomer into polyethylene terephthalate, already leads into ranges of elastoplastics. Thus, copolymers which can be processed easily and have desirable flexibility, elasticity and toughness properties can be obtained with the compounds according to the invention.

COMPARISON EXAMPLE: Copolyethylene terephthalate containing 20 mol % of 4,4'-bis-[3-(5'-methoxycarbonyl-n-pentyl)hydantoin-1-yl]-diphenylmethane For comparison, a heterocyclic dicarboxylic acid alkyl ester described in DT-OS Nos. 1,906,492 and 2,358,437 is used for the production of a copolyethylene terephthalate. For this purpose a mixture of 11.65 g (0.06 mol) of dimethyl terephthalate, 12.50 g (0.2 mol) of ethylene glycol and 9.73 g of 4,4'-bis-[3-(5'-methoxycarbonyl-n-pentyl)-hydantoin-1-yl]-diphenylmethane is trans-esterified and subjected to a polycondensation reaction, under the catalytic action of 0.01 g of calcium acetate, 0.015 g of zinc acetate, 0.007 g of manganese-II acetate and 0.04 g of antimony trioxide, as follows:

2 hours at 150° C. → 200° C./$N_2$/normal pressure
2 hours at 200° C. → 240° C./$N_2$/normal pressure
35 minutes at 240° C. → 280° C./90 mm Hg → 14 mm Hg
30 minutes at 280° C./0.2–0.3 mm Hg.

The desired copolyester is obtained in the form of a black-brown, amorphous product which softens at 75° C. and has a relative viscosity of 2.17.

Glass transition range: 63°–75° C.
the product is amorphours, no crystallite melting point can be determined with DSC
decomposition temperature: about 350° C.

The product is processed in the customary manner (Arburg Allrounder 100 M) to standard small bars which have the following properties:

impact bending strength (DIN 53,453): 8.7 kp cm/cm$^2$

These results show that the copolyesters with 4,4'-bis-[3-(5'-methoxycarbonyl-n-pentyl)-hydantoin-1-yl]-diphenylmethane are not suitable for applications for which products which have a high toughness at room temperature are required. Copolyethylene terephthalates which have the properties of elastoplastics cannot be obtained even with the incorporation of larger amounts of this comonomer, which, moreover, is more difficult to carry out, than in the case of the dicarboxylic acid alkyl esters according to the invention.

What is claimed is:
1. A dicarboxylic acid or dicarboxylic acid ester of the formula I

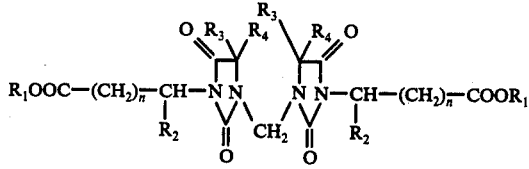

(I)

wherein both $R_1$ independently of one another each denote hydrogen, alkyl with 1 to 4 C atoms or phenyl, both $R_2$ each denote hydrogen or alkyl with 1 to 10 C atoms and, if the two $R_2$ each denote hydrogen, the two $n$ represent identical or different numbers from 2 to 12 and, if the two $R_2$ each denote an alkyl group with 1 to 10 C atoms, the two $n$ represent identical or different numbers from 1 to 12, $R_3$ denotes hydrogen, methyl or ethyl and $R_4$ denotes methyl, ethyl, propyl or isopropyl.

2. A dicarboxylic acid or dicarboxylic acid ester according to claim 1, wherein in the formula I both $R_1$ independently of one another each denote hydrogen, alkyl with 1 to 4 C atoms or phenyl, both $R_2$ independently of one another each denote hydrogen or alkyl with 1 to 10 C atoms, $R_3$ denotes hydrogen, methyl or ethyl and $R_4$ denotes methyl, ethyl, propyl or isopropyl and the two $n$ denote identical or different numbers from 2 to 12.

3. A compound according to claim 1 wherein $R_1$ is alkyl of 1 to 4 carbon atoms or phenyl, $R_2$ is hydrogen and $n$ is a number from 2 to 4.

4. A compound according to claim 1 wherein $R_1$ is methyl, ethyl or phenyl, $R_2$ is hydrogen, $R_3$ is methyl, $R_4$ is methyl or ethyl and $n$ is a number from 2 to 4.

5. A compound as claimed in claim 1, which is 1,1'-methylene-bis-[3-(3'-methoxycarbonyl-n-propyl)-5,5-dimethylhydantoin].

6. A compound as claimed in claim 1, which is 1,1'-methylene-bis-[3-(3'-phenoxycarbonyl-n-propyl)-5,5-dimethylhydantoin].

7. A compound as claimed in claim 1, which is 1,1'-methylene-bis-[3-(3'-methoxycarbonyl-n-propyl)-5-isopropylhydantoin].

8. A compound as claimed in claim 1, which is 1,1'-methylene-bis-[3-(3'-ethoxycarbonyl-n-propyl)-5,5-dimethylhydantoin].

9. A compound as claimed in claim 1, which is 1,1'-methylene-bis-[3-(3'-butoxycarbonyl-n-propyl)-5-isopropylhydantoin].

10. A compound as claimed in claim 1, which is 1,1'-methylene-bis-[3-(4'-methoxycarbonyl-n-butyl)-5,5-dimethylhydantoin].

11. A compound as claimed in claim 1, which is 1,1'-methylene-bis-[3-(5'-methoxycarbonyl-n-pentyl)-5,5-dimethylhydantoin].

12. A compound as claimed in claim 1, which is 1,1'-methylene-bis-[3-(10'-methoxycarbonyl-n-decyl)-5,5-dimethylhydantoin].

13. A compound which is 1,1'-methylene-bis-[3-(1'-dodecyl-1'-methoxycarbonyl-methyl)-5,5-dimethylhydantoin].

* * * * *